(12) United States Patent
Sager et al.

(10) Patent No.: US 8,987,190 B2
(45) Date of Patent: Mar. 24, 2015

(54) TREATMENT OF ACUTE ISCHEMIC STROKE OR INTRACRANIAL BLEEDING WITH TPA AND CARBAMYLATED ERYTHROPOIETIN

(75) Inventors: Thomas Nikolaj Sager, Smorum (DK); Michael Chopp, Southfield, MI (US); Zheng Gang Zhang, Troy, MI (US)

(73) Assignee: H. Lundbeck A/S, Valby (DK)

( * ) Notice: Subject to any disclaimer, the term of this patent is extended or adjusted under 35 U.S.C. 154(b) by 325 days.

(21) Appl. No.: 13/510,560

(22) PCT Filed: Nov. 15, 2010

(86) PCT No.: PCT/DK2010/050306
§ 371 (c)(1),
(2), (4) Date: Apr. 15, 2013

(87) PCT Pub. No.: WO2011/060789
PCT Pub. Date: May 26, 2011

(65) Prior Publication Data
US 2013/0259853 A1    Oct. 3, 2013

Related U.S. Application Data

(60) Provisional application No. 61/262,390, filed on Nov. 18, 2009.

(30) Foreign Application Priority Data

Nov. 18, 2009    (DK) ................................ 2009 01223

(51) Int. Cl.
*A61K 38/18*    (2006.01)
*A61K 38/00*    (2006.01)
*A61K 38/49*    (2006.01)
*A61K 38/48*    (2006.01)

(52) U.S. Cl.
CPC ............... *A61K 38/482* (2013.01); *A61K 38/49* (2013.01); *A61K 38/1816* (2013.01)
USPC ........... 514/1.1; 514/7.7; 514/13.5; 514/14.7; 530/350

(58) Field of Classification Search
None
See application file for complete search history.

(56) References Cited

FOREIGN PATENT DOCUMENTS

| DK | PA200901223 | 11/2010 |
|----|-------------|---------|
| WO | WO 2006/050819 | 5/2006 |
| WO | WO 2009/088572 | 7/2009 |
| WO | WO 2011/060789 | 5/2011 |

OTHER PUBLICATIONS

Paul Lapchak (Expert Opin Investig Drugs 2010, 19:10, 1179-1186).*
Bath, P. (2011) "Clot-Busting for Stroke," The Lancet 377:1643-1644.
Benedict, C.R. et al. (1995) "New Variant of Human Tissue Plasminogen Activator (TPA) With Enhanced Efficacy and Lower Incidence of Bleeding Compared With Recombinant Human TPA," Circulation 92:3032-3040.
Cheng, Y.D. et al. (2004) "Neuroprotection for Ischemic Stroke: Two Decades of Success and Failure," NeuroRx: J. Amer. Soc. Exper. NeuroTherap. 1:36-45.
H Lundbeck A/S Response the Communication pursuant to Article 94(3) EPC issued Oct. 5, 2013 for European patent application No. 10781412.1 (6 pages).
Hacke, W. et al. (2008) "Thrombolysis with Alteplase 3 to 4.5 Hours after Acute Ischemic Stroke," 359(33):1317-1329.
López-Atalaya, J.P. et al. (2007) "Recombinant Desmodus rotundus Salivary Plasminogen Activator Crosses the Blood-Brain Barrier Through a Low-Density Lipoprotein Receptor-Related Protein-Dependent Mechanism Without Exerting Neurotoxic Effects," Stroke 38:1036-1043.
Ogawa, A. et al.(2007) "Randomized Trial of Intraarterial Infusion of Urokinase Within 6 Hours of Middle Cerebral Artery Stroke: The Middle Cerebral Artery Embolism Local Fibrinolytic Intervention Trial (MELT) Japan," Stroke 38:2633-2639.
Lapchak, P.A. et al. (Epub Aug. 16, 2008) "Therapeutic Window for Nonerythropoietic Carbamylated-Erythropoietin to Improve Motor Function Following Multiple Infarct Ischemic Strokes in New Zealand White Rabbits," Brain Res. 1238:208-214.
Lapchak, P.A. (2008) "Carbamylated Erythropoietin to Treat Neuronal Injury: New Development Strategies," Expert Opin. Investig. Drugs. 17(8):1175-1186.
Lapchak, P.A. (2008) "The Many Faces of Erythropoietin: From Erythropoiesis to a Rational Neuroprotective Strategy—Correspondence," Expert Opin. Investig. Drugs. 17(10):1615-1616.
Leist, M. et al. (2004) "Derivatives of Erythropoietin That are Tissue Protective but not Erythropoietic," Science. 305(5681):239-242.
Ehrenreich H. et al. (2002) "Erythropoietin Therapy for Acute Stroke is Both Safe and Beneficial," Mol Med. 8(8):495-505.
D'Olhaberriague, L. et al. (2000) "Tissue Plasminogen Activator for Acute Ischemic Stroke in Patients with Unruptured Cerebral Aneurysms," J. Stroke Cerebrovascular Dis. 9(4):181-184.
Ehrenreich H. et al. (Epub Oct. 15, 2009) "Recombinant Human Erythropoietin in the Treatment of Acute Ischemic Stroke," Stroke 40(12):e647-e656.
International Search Report for PCT/DK2010/050306 (Jun. 22, 2011) (6 pages).

* cited by examiner

*Primary Examiner* — James H Alstrum Acevedo
*Assistant Examiner* — Li Lee
(74) *Attorney, Agent, or Firm* — William C. Schrot; Jeffrey I. Auerbach; AuerbachSchrot LLC

(57) ABSTRACT

The present invention relates a method for the treatment of intracranial bleeding comprising administration of a therapeutically effective amount of tPa and a therapeutically effective amount of carbamylated erythropoietin.

9 Claims, 2 Drawing Sheets

|  | blood volume | | |
| --- | --- | --- | --- |
|  | N | Mean | Std |
| CEPO combination | | | |
| 1. Control | 10 | 2.73 | (2.51) |
| 2 tPA alone (3h) | 10 | 4.25 | (3.80) |
| 3. CEPO alone (3h) | 10 | 3.34 | (2.23) |
| 4. tPA+CEPO (3h) | 10 | 0.63 | (1.07) |
| EPO Combination | | | |
| 1. Control | 10 | 2.73 | (2.51) |
| 2 tPA alone (3h) | 10 | 4.25 | (3.80) |
| 3. EPO alone (3h) | 10 | 4.56 | (1.90) |
| 4. tPA+EPO (3h) | 10 | 4.63 | (2.93) |

Fig. 2

SEQUENCE LISTING

```
<160> NUMBER OF SEQ ID NOS: 2

<210> SEQ ID NO 1
<211> LENGTH: 166
<212> TYPE: PRT
<213> ORGANISM: Homo sapiens
<220> FEATURE:
<221> NAME/KEY: MISC_FEATURE
<223> OTHER INFORMATION: Erythropoietin

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140
```

```
Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 2
<211> LENGTH: 165
<212> TYPE: PRT
<213> ORGANISM: Homo sapiens
<220> FEATURE:
<221> NAME/KEY: MISC_FEATURE
<222> LOCATION: (1)..(165)
<223> OTHER INFORMATION: Truncated EPO without R166

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp
                165
```

TREATMENT OF ACUTE ISCHEMIC STROKE OR INTRACRANIAL BLEEDING WITH TPA AND CARBAMYLATED ERYTHROPOIETIN

CROSS-REFERENCE TO RELATED APPLICATIONS

This Application is a §371 national application of International Application No. PCT/DK2010/050306 (filed on Nov. 15, 2010; pending), which application claims priority to U.S. Patent Application Ser. No. 61/262,390 (filed on Nov. 18, 2009) and Danish Patent Application Serial No. PA200901223 (filed on Nov. 18, 2009), all of which applications are herein incorporated by reference in their entireties.

FIELD OF THE INVENTION

The present invention relates a method for treating acute ischemic stroke and/or intracranial bleeding in a patient in the need thereof comprising administration of a therapeutically effective amount of tPa and a therapeutically effective amount of carbamylated erythropoietin.

BACKGROUND OF THE INVENTION

Stroke ranks second after ischemic heart diseases as cause of lost disability-adjusted life-years in high-incomes countries and as cause of death worldwide (Lopez et al., Lancet 2006; 367:1747-57).

Different clinical pictures summarized under the term "stroke", which term describe a disturbance in the blood supply to the brain. This can be due to ischemia (lack of blood supply) caused by thrombosis or embolism or due to a hemorrhage.

An ischemia insult results in damages to tissues or organs in the affected area as a result from a cascade of events from energy depletion to cell death. Intermediate factors include an excess of extracellular excitatory amino acids, free radical formation and inflammation. Immediately after arterial occlusion, a central core of very low perfusion is surrounded by an area of dysfunction caused by metabolic and ionic disturbances, but in which structural integrity is preserved. In the first minutes to hours the clinical deficits do not necessary result in irreversible damage. It is therefore of outmost importance to reduce the time wherein the tissues receive low perfusion.

Approved therapeutic approaches to treat arterial thrombosis, such as a cerebral stroke, use plasminogen activators alone or in combination with antiplatelet drugs and anticoagulants.

Approved plasminogen activators currently used in acute ischemic stroke include only tissue-type plasminogen activator ("tPa"). Administration of tPa in the setting of occlusive thrombus enhances the rate of fibrin degradation, restoring arterial patency and blood flow to ischemic tissues.

Plasminogen activators are enzymes that activate the zymogen plasminogen to generate the serine proteinase plasmin, which degrades fibrin.

Tissue-type plasminogen activator is a fibrin specific activator of plasminogen and an effective thrombolytic agent, which primary application is in the clinic for the treatment of heart attack and stroke.

Natural tissue-type plasminogen has a plasma half-life of about six minutes or less. Due to its rapid clearance from the circulation, tPa is usually infused to achieve thrombolysis. Front loaded dosing with increased concentrations of tPa has shown more rapid and complete lysis compared to the standard infusion protocol and early potency is correlated with improved survival rate.

tPa is commercially marketed as recombinant alteplase (under tradename such as Actilyse® or Activase®) by Boehringer Ingelheim. In USA FDA has approved a dose of 0.9 mg/kg with a maximum of 90 mg in acute ischemic stroke. Activase® is administered as infusion over 60 minutes with 10% of the total dose administered as an initial intravenous bolus dose over 1 minute.

The treatment should be initiated within 3 hours after onset of stroke symptoms. However recent data prolongs this period to 4.5 hours since onset of stroke symptoms. The reason for this time restriction is due to an increasing occurrence of side effects, most notably intracranial hemorrhage, which has constrained its clinical use.

Another suggested strategy to treat acute ischemic stroke has been to administer erythropoietin (EPO), because EPO has been shown to have both neuroprotective and neurogenerative effects. However, in a recent clinical study in the treatment of acute ischemic stroke it was shown that patients receiving both erythropoietin (EPO) and tPa had an increased mortality (Hannelore et al., 2009; published online by Stroke, October 2009). This finding was somewhat unexpected because it was believed that a beneficial effect could result from combining tPa (due to its clot-dissolving propertied) and EPO (which would salvage potentially viable brain tissue). However, the clinical trial showed that a combination of EPO and tPa was not advantageous.

A new drug under the development for acute ischemic stroke is carbamylated erythropoietin (CEPO). It is chemically modified EPO by carbamylation of lysine residues (Leist et al. Science. 2004; 305(5681):239-42 hereby incorporated by reference in its entirety) which has the advantage of not binding to the erythropoietin receptor and is thereby without haematopoietic side effects. Despite the lack of binding to the erythropoietin receptor, CEPO retains full cytoprotective properties, demonstrating that CEPO mediates its beneficial effects via a mechanism different from that of the classical erythropoietin receptor.

In the present application, it has been confirmed that EPO, tPa and the combination of EPO and tPa treatment increased the intracranial bleeding compared to saline injections. Surprisingly, however, the inventors found a combined treatment with tPa and CEPO in a stroke model reduced cerebral hemorrage.

The object of the present invention is therefore to provide an improved treatment regime which reduces the haemorrhaging while at the same time effectively lysis the clot and re-establish perfusion to the affected areas.

SUMMARY OF THE INVENTION

The invention provides carbamylated erythropoietin (CEPO) and tissue-type plasminogen activator (tPa) in the treatment of an acute ischemic stroke.

In another aspect of the invention is provided CEPO and tPa for use in the treatment of intracranial bleeding.

In a further aspect of the invention is provided a method for the treatment of acute ischemic stroke in a patient in the need thereof comprising the administration of a therapeutically effective amount of CEPO and a therapeutically effective amount of tPa.

In still further aspect of the invention is provided a method for the treatment of intracranial bleeding in a patient in the need thereof comprising the administration of a therapeutically effective amount of CEPO and a therapeutically effective amount of tPa.

In a still further aspect of the invention is provided a pharmaceutical composition comprising a therapeutically effective amount of CEPO and a therapeutically effective amount of tPa, and a pharmaceutically acceptable carrier.

In a last aspect is described a kit comprising said CEPO and said tPa

BRIEF DESCRIPTION OF DRAWINGS

FIG. 2 shows the mean blood volume lost in 4 treatment groups.

DETAILED DESCRIPTION OF THE INVENTION

Figure 1:
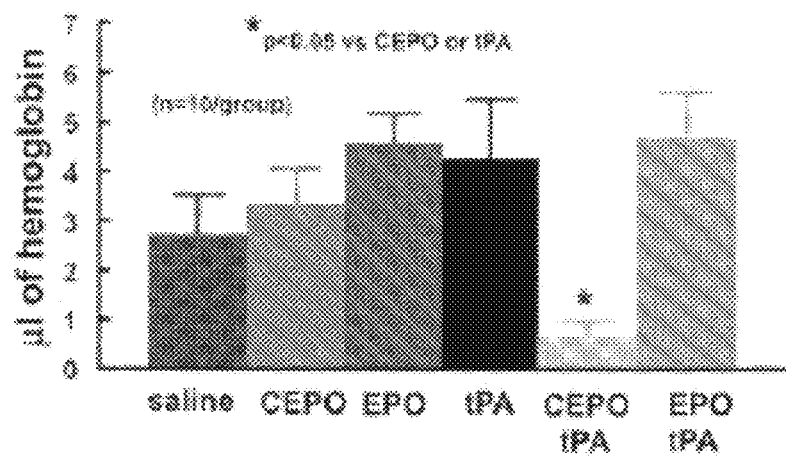
FIG. 1 shows haemoglobin levels (μl) in the ipsilateral hemisphere 24 hours after occlusion of the middle cerebral artery in male Wistar rats. The treatment was initiated after 3 hours after middle cerebral artery occlusion.

Cerebral ischemic insults (ischemia) are characterized in a reduction or interruption of the blood circulation in the brain due to a lack of arterial blood supply. Often this is caused by thrombosis of an arteriosclerotic vessel or by cardial embolisms.

Haemorrhagic insults are the result of perforation of brain supplying arterias. However, only about one fifth of all cerebral insults are caused by haemorrhagic insults and stroke due to thrombosis is therefore a much more common cause of ischemic insults.

Ischemia of the neuronal tissue in the brain usually results in necrosis of neural cells in the effected area. Necrosis in neuronal tissue is a complex cascade affected by factors such as a lack of oxygen, energy depletion, excess of extracellular excitatory amino acids, free radical formation and inflammation.

In order to re-establish the blood supply and limit the damages to the surrounding tissues re-opening of the closed vessel is an important factor in the therapy of acute cerebral ischaemia. In the body, the naturally occurring fibrinolysis is based on the proteolytic activity of the serine protease plasmin which originates from its inactive precursor by catalysis (activation). The natural activation of plasminogen is catalyzed by the plasminogen activators u-PA (urokinase type plasminogen activator) and t-PA (tissue plasminogen activator).

Extensive experience on therapeutic thrombolysis is available for the tissue type plasminogen activator (tPa or recombinant tPa (rtPa)) and so far the therapy with tPa is the only treatment of acute cerebral ischaemia approved by the Food and Drug Administration in USA. However, treatment with tPa is restricted to an application within 3 hours after the onset of stroke, because treatment with tPa is associated with a risk of intracranial haemorrhage or subarachnoid haemorrhage. Treatment with tPa within 3 hours after the onset of symptoms will rescue one in ten patients from disability but will cause a serious haemorrhagic conversion in one out of 20 patients. Risk of death upon treatment is approximately one in 100.

Recently, however, a new science advisory from the American Heart Association/American Stroke Association has given the green light to the use of tPa to treat acute ischemic stroke between 3 and 4.5 hours after symptom onset.

The term "therapeutically effective amount" as used herein shall mean that amount of a CEPO and/or tPa that will elicit the biological or medical response of a mammal that is being sought by a researcher or clinician. The therapeutically effective amount will depend on the condition to be treated, the route and duration of administration, the physical attributes of the mammal, including body weight, and whether other medications are being taken concurrently, and may be determined according to methods well known to those skilled in the art in light of the present disclosure.

tPa is usually given in doses below 150 or 100 mg. In acute ischemic stroke the maximal dose is in total 90 mg given intravenously (i.v.) as infusion over a time period of 60 minutes.

The current approved treatment regime for Activase (alteplase) is an administration of a about 0.9 mg/kg body weight administered as infusion over approximately 60 minutes, with about 10% of the total dose administered as an initial intravenous bolus dose over approximately 1 minute.

Another strategy to treat acute ischemic stroke has been to treat the patients with EPO because of EPO's neuroprotective/neuroregenerative properties (Ehrenreich et al., Molecular Medicine, 2002; 8:495-505). However, a recent publication by Ehrenreich (Stroke 2009, online publication) showed that patients receiving tPa in addition to the prescribed EPO treatment suffered from an increased death rate. This finding is in line with the findings by the inventors of present invention who have observed that a combination treatment of EPO and tPa in an animal model of acute ischemic stroke resulted in a increased intracranial haemorrhage.

However, when carbamylated erythropoietin (CEPO) is used in a combinational therapy with tPa the intracranial bleeding is reduced considerably, both compared to monotherapy of CEPO and tPa and the combination therapy with EPO and tPa.

The invention thus relates to CEPO and tPa for use in the treatment of acute ischemic stroke. Another aspect of the invention relates to CEPO and tPa for use in the treatment of intracranial bleeding e.g. due to the fibrinolytic treatment and/or ischemic insult in the brain, such as an acute ischemic stroke. In both aspects, CEPO and tPa may be given parentally, such as by i.v. administration (e.g. infusion), either simultaneously, separately and/or sequentially.

According to one embodiment of the invention CEPO may be administered at a dose ranging from about 0.5 μg/kg body weight to about 50 μg/kg body weight, such as e.g. a dose ranging from about 0.5 μg/kg body weight to about 10 μg/kg body weight, a dose ranging from about 10 μg/kg body weight to about 15 μg/kg body weight, a dose ranging from about 15 μg/kg body weight to about 20 μg/kg body weight, a dose ranging from about 20 μg/kg body weight to about 25 μg/kg body weight, a dose ranging from about 25 μg/kg body weight to about 30 μg/kg body weight, a dose ranging from about 30 μg/kg body weight to about 35 μg/kg body weight, a dose ranging from about 35 μg/kg body weight to about 40 μg/kg body weight, a dose ranging from about 40 μg/kg body weight to about 45 μg/kg body weight, a dose ranging from about 45 μg/kg body weight to about 50 μg/kg body weight. In an embodiment the dose is about 0.5 μg/kg body weight, about 5 μg/kg body weight or about 50 μg/kg body weight. tPa may be administered simultaneously, separate and/or sequentially in a dose of about 0.9 mg/kg body weight, such as e.g. about 0.5 mg/kg to about 1.2 mg/kg or about 0.8 mg/kg to about 1 mg/kg, e.g. infused i.v. over approximately 60 minutes, with about 10% of the total dose administered as an initial intravenous bolus dose over approximately 1 minute. According to one embodiment the maximal dose administered is of about 90 mg.

The treatment may be initiated within the 4.5 hours since onset of stroke symptoms as for tPa, however, due to the decreased bleeding of tPa in combination with CEPO the time window may be expanded so that there is no time limit for the start of treatment. The time window may thus be expanded so the treatment can be initiated within about 10 hours since onset of stroke, such as e.g. within about 5 hours, within about 5.5 hours, within about 6 hours, within about 6.5 hours, within about 7 hours, within about 7.5 hours, within about 8 hours, within about 8.5 hours, within about 9 hours or within about 9.5 hours since onset of stroke.

Further embodiments of the invention are evident from the claims and the example.

The present invention also relates to a kit tPa and CEPO. The kit may in one embodiment be for the treatment of acute ischemic stroke or intracranial bleeding e.g. associated with the fibrinolytic treatment and/or the ischemic insult. Such kit may be valuable in emergency settings or in an ambulance or other places remote from a hospital.

In the present invention, the term CEPO is intended to include any variant or derivative of carbamylated EPO (e.g described in U.S. 2004157293 or Science, Vol. 35, pp 239-242 or WO 2006/050819 hereby incorporated by reference in their entirety), that is a variant or derivative of EPO in which at least one of the primary-amino groups (the lysines and the N-terminal group) of the protein is carbamylated. In particular, the invention relates to CEPO with an amino acid sequence as depicted below in table 1 (SEQ ID NO 2) or comprising an additional arginine in the C-terminal end (SEQ ID NO 1), or a sequence which is 95%, 98% or 99% identical to SEQ ID NO 1 or 2.

TABLE 1

Potential carbamylation sites are shown in bold and conventional amino acids in arial font.

| | | | | | | | | | | | | | | | | | | | |
|---|---|---|---|---|---|---|---|---|---|---|---|---|---|---|---|---|---|---|---|
| 1 | A | P | P | R | L | I | C | D | S | R | V | L | E | R | Y | L | L | E | A K |
| 21 | E | A | E | N | I | T | T | G | C | A | E | H | C | S | L | N | E | N | I T |
| 41 | V | P | D | T | K | V | N | F | Y | A | W | K | R | M | E | V | G | Q | Q A |
| 61 | V | E | V | W | Q | G | L | A | L | L | S | E | A | V | L | R | G | Q | A L |
| 81 | L | V | N | S | S | Q | P | W | E | P | L | Q | L | H | V | D | K | A | V S |
| 101 | G | L | R | S | L | T | T | L | L | R | A | L | G | A | Q | K | E | A | I S |
| 121 | P | P | D | A | A | S | A | A | P | L | R | T | I | T | A | D | T | F | R K |
| 141 | L | F | R | V | Y | S | N | F | L | R | G | K | L | K | L | Y | T | G | E A |
| 161 | C | R | T | G | D | | | | | | | | | | | | | | |

There are nine potential carbamylation sites as shown in table 1: Alanine at position 1 and Lysine at positions 20, 45, 52, 97, 116, 140, 152 and 154. Accordingly, the invention relates to CEPO in which at least one or more of the of the amino acids selected from the group comprising alanine at position 1 and lysine at positions 20, 45, 52, 97, 116, 140, 152 and 154 (as shown in table 1) are carbamylated.

CEPO may be produced by carbamylating EPO e.g. as disclosed in WO2006/002646. Briefly, purified human EPO (or alternatively recombinant human EPO or biologically or chemically modified human EPO) can be mixed with an approximately equal volume of 1M potassium cyanate/ 0.25M potassium tetraborate, pH about 9.0, and incubating at about 29° C. for about 24-48 hours. The reaction can be stopped by cooling to room temperature, adding 3M ammonium sulphate/150 mM Tris-HCl, pH 7.5 and hydrophobic interaction chromatography (HIC).

CEPO and tPa may be comprised in a pharmaceutical composition. The pharmaceutical compositions of the invention may comprise a therapeutically effective amount of CEPO and tPa and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of CEPO and/or tPa, preferably in purified form, together with a suitable amount of carrier so as to provide the form for proper administration to the patient. The formulation should suit the mode of administration.

Pharmaceutical compositions adapted for parenteral administration include aqueous and non-aqueous sterile injectable solutions or suspensions, which may contain antioxidants, buffers, bacteriostats, and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules, and tablets. In one embodiment, an autoinjector comprising an injectable solution of a compound of the invention may be provided for emergency use by ambulances, emergency rooms.

In a preferred embodiment, the composition is formulated in accordance with routine procedures as a pharmaceutical composition adapted for intravenous administration to human beings. Typically, compositions for intravenous administration are solutions in sterile isotonic aqueous buffer.

Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration. In a particular embodiment, the pharmaceutical composition comprising CEPO and tPa is for use in the treatment of intracranial bleeding.

EXAMPLES

Example 1

Comparison of hemorrhage transformation between CEPO and tPa treatment and EPO and tPa treatment when the treatment is initiated 3 hours after embolic middle cerebral artery occlusion.

Materials: Wistar rats n=60

Methods: Male Wistar rats (3 months old) were subjected to an embolic middle cerebral artery occlusion. After embolic middle cerebral artery (MCA) occlusion, rats were randomly divided into six groups (n=10 rats/group) and treatment was initiated 3 h after MCA occlusion:

1) saline at 3 hours+vehicle at 3 hours
2) tPa (10 mg/kg, i.v., at 3 hours)+epo (42 µg/kg, i.v., at 3 hours)
3) tPa (10 mg/kg, i.v., at 3 hours)+CEPO (50 µg/kg, i.v., at 3 hours)
4) tPa (10 mg/kg, i.v., at 3 hours)+vehicle (at 3 hours)
5) saline (at 3 hours)+CEPO (50 µg/kg, i.v. at 3 hours)
6) saline (at 3 hours)+EPO (42 µg/kg, i.v., at 3 hours)

Twenty-four hours after MCA occlusion, rats were anesthetized and their brains were perfused with saline. The contralateral and ipsilateral hemispheres were isolated and levels of hemoglobin in the each hemisphere were measured at 540 nm with a spectrophotometer. Hemoglobin volume (µL) was obtained by comparison with a standard curve.

The 2×2 factorial design and 2-way ANOVA were considered for monotherapy EPO/CEPO and combination tPa-EPO/CEPO treatments. The analysis started testing for overall group effect/treatment interactions, followed by the pair-wise group comparisons if the overall group effect/treatment interaction was detected at the 0.05 level; otherwise the pair-wise group comparisons would be considered as exploratory analysis. Results are shown in FIGS. 1 and 2.

CONCLUSION

The study showed that the combination of CEPO with tPa significantly reduced brain hemorrhage compared to the monotherapy of CEPO or tPa, when the treatment was initiated 3 hours after MCA occlusion.

---

The invention claimed is:

1. A method for treatment of intracranial bleeding in a patient in the need thereof comprising administration of a therapeutically effective amount of tissue-type plasminogen activator (tPa) and a therapeutically effective amount of carbamylated erythropoietin (CEPO), wherein said carbamylated erythropoietin has the sequence of SEQ ID NO 1 or SEQ ID NO 2.

2. The method according to claim 1, wherein the intracranial bleeding is due to fibrinolytic treatment and/or due to an ischemic insult in the brain.

3. The method according to claim 1, wherein the dose of CEPO ranges from 0.5 µg/kg body weight to about 50 µg/kg body weight.

4. The method according to claim 3, wherein tPa is administered at a dose of about 0.9 mg/kg body weight.

5. The method according to claim 1, wherein the administration of tPa and CEPO is simultaneous, separate and/or sequential.

6. A pharmaceutical composition comprising a therapeutically effective amount of tissue-type plasminogen activator (tPa) and a therapeutically effective amount of carbamylated erythropoietin (CEPO), wherein said carbamylated erythropoietin has the sequence of SEQ ID NO 1 or SEQ ID NO 2, and a pharmaceutically acceptable carrier.

7. The pharmaceutical composition according to claim 6, wherein the carrier is a diluent, an adjuvant or an excipient.

8. A method of treating intracranial bleeding or acute ischemic stroke in a patient in need thereof, comprising administering the pharmaceutical composition of claim 6.

9. A kit comprising CEPO and tPa according to claim 6.

* * * * *